(12) United States Patent
Casu et al.

(10) Patent No.: US 6,197,943 B1
(45) Date of Patent: Mar. 6, 2001

(54) GLYCOSAMINOGLYCANS HAVING HIGH ANTITHROMBOTIC ACTIVITY

(75) Inventors: Benito Casu, Milan; Annamaria Naggi, Legnano; Giangiacomo Torri, Milan, all of (IT)

(73) Assignee: Inalco S.p.A., Milan (IT)

( * ) Notice: Subject to any disclaimer, the term of this patent is extended or adjusted under 35 U.S.C. 154(b) by 0 days.

(21) Appl. No.: 09/381,451

(22) PCT Filed: Mar. 24, 1998

(86) PCT No.: PCT/EP98/01714

§ 371 Date: Sep. 20, 1999

§ 102(e) Date: Sep. 20, 1999

(87) PCT Pub. No.: WO98/42754

PCT Pub. Date: Oct. 1, 1998

(30) Foreign Application Priority Data

Mar. 24, 1997 (IT) ............................................... MI97A0678

(51) Int. Cl.⁷ ............................ C08B 37/10; A01N 43/04
(52) U.S. Cl. ............................... 536/21; 514/56; 514/822; 536/124
(58) Field of Search ...................... 514/56, 822; 536/21, 536/124

(56) References Cited

U.S. PATENT DOCUMENTS

| | | | |
|---|---|---|---|
| 4,281,108 | * | 7/1981 | Fussi ........................................ 536/21 |
| 4,727,063 | * | 2/1988 | Naggi et al. ............................. 514/56 |
| 4,761,401 | * | 8/1988 | Couchman et al. ..................... 514/53 |
| 5,008,253 | * | 4/1991 | Casu et al. .............................. 514/54 |
| 5,013,724 | * | 5/1991 | Petitou et al. ........................... 514/54 |
| 5,071,969 | * | 12/1991 | van Boeckel et al. ................ 536/1.1 |
| 5,164,378 | * | 11/1992 | Conti et al. ............................... 514/56 |
| 5,550,116 | * | 8/1996 | Lormeau et al. ........................ 514/56 |
| 5,599,801 | * | 2/1997 | Branellec et al. ....................... 514/56 |

OTHER PUBLICATIONS

Carbohydrate Chemistry. edited by John F. Kennedy, published by Clarendon Press, pp. 330–332, 1988.*

Casu, B. "Structure of Heparin and Heparin Fragments." Annals of the New York Academy of Sciences (Heparin and Related Polysaccharides) ed. by Ofosu et al., vol. 556, pp. 1–17, Jun. 1989.*

Conrad, H. "Structure of Heparan Sulfate and Dermatan Sulfate." Annals of the New York Academy of Sciences (Heparin and Related Polysaccharides), ed. by Ofosu et al., vol. 556, pp. 18–28, Jun. 1989.* van Boeckel et al. "Structure–Activity Relationships of Synthetic Heparin Fragments." Annals of the New York Academy of Sciences (Heparin and Related Polysaccharides), ed. by Ofosu et al., vol. 556, pp. 489–491, Jun. 1989.*

Roden et al. "Heparin—An Introduction." Heparin and Related Polysaccharides. edited by Lane et al., published by Plenum Press, pp. 1–20, 1992.*

Petitou, M. "Chemical Synthesis and Hemisynthesis in the Field of Glycosaminoglycans." Heparin and Related Polysaccharides. edited by Lane et al., published by Plenum Press, pp. 21–30, 1992.*

Barrowcliffe, T.W. "LMW Heparin: Relaionship Between Antithrombotic and Anticoagulant Effects." Heparin and Related Polysaccharides. edited by Lane et al., published by Plenum Press, pp. 205–220, 1992.*

Hemker et al. "The Mode of Action of Heparins in Vitro and in Vivo." Heparin and Related Polysaccharides. edited by Lane et al., published by Plenum Press, pp. 221–230, 1992.*

Boneu et al. "Pharmacokinetics of Heparin and of Dermatan Sulfate: Clinical Implications." Heparin and Related Polysaccharides. edited by Lane et al., published by Plenum Press, pp. 237–247, 1992.*

Bergqvist et al. "Glycosaminoglycans in Prophylaxis Against Venous Thromboembolism." Heparin and Related Polysaccharides. edited by Lane et al., published by Plenum Press, pp. 259–274, 1992.*

Samama, M. "Treatment of Deep Vein Thrombosis (DVT) with Low Molecular Weight Heparins (LMWH)." Heparin and Related Polysaccharides. edited by Lane et al., published by Plenum Press, pp. 275–281, 1992.*

Polysaccharides in Medicinal Applications. edited by Severian Dumitriu, published by Marcel Dekker, Inc., pp. 556–567, 1996.*

Heparin–Binding Proteins. edited by H. Edward Conrad, published by Academic Press, (Chapter 7—Heparinoid/Protein Interactions), pp. 183–202, 1998.*

Pinhal et al. "Antithrombotic Agents Stimulate the Synthesis and Modify the Sulfation Pattern of a Heparan Sulfate Proteoglycan from Endothelial Cells." Thrombosis Research, vol. 74, No. 2, pp. 143–153, 1994.*

Hurley et al. "Structural Determinants of the Capacity of Heparin to Inhibit Collagen." J. Bone Mineral. Res., vol. 5 No. 11, pp. 1127–1134, 1990.*

Naggi et al., "Supersulfated' heparin fragments, a new type of low–molecular weight heparin. Physicochemical and pharmacological properties." Biochem. Pharmacol., vol. 36(12), pp. 1895–1900, 1987.*

Abstract of JP 04 202 401 A (Terumo Corp.), XP–002075693, Jul. 23, 1992.

The Journal of Biochemistry, vol. 108, No. 4, 1990, pp. 588–592, XP002075691, "Generation of Affinity for Antithrombin III by Supplemental Sulfation of Heparin Species with Low Affinity for the Protein", A. Ogamo et al.

Methods in Carbohydrate Chemistry, vol. 8, 1980, pp. 287–289, XP002075692, "Desulfation of Glycosaminoglycuronan Sulfates", N. Kinzo et al.

* cited by examiner

*Primary Examiner*—Howard C. Lee
(74) *Attorney, Agent, or Firm*—Hedman & Costigan, P.C.

(57) ABSTRACT

Glycosaminoglycans having high antithrombotic activity in vitro, obtained by various kinds of glycosaminoglycans supersulfated by the preparation of the salt of an organic base of the starting supersaturated glycosaminoglycan, by partial solvolytic desulfation of said salt and N-resulfation of said partially desulfated product.

5 Claims, 2 Drawing Sheets

GLYCOSAMINOGLYCANS HAVING HIGH ANTITHROMBOTIC ACTIVITY

FIELD OF THE INVENTION

Figure 1A:
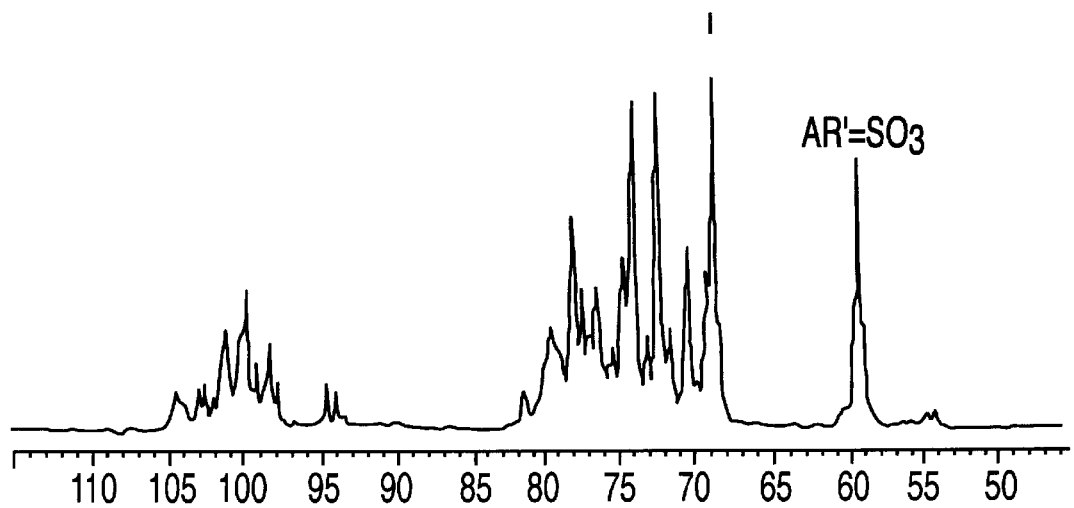

Object of the present invention are glycosaminoglycans having high antithrombotic activity in vitro, obtained by various kinds of glycosaminoglycans supersulfated by the preparation of the salt of an organic base of the starting supersulfated glycosaminoglycan, by partial solvolytic desulfation of said salt and N-resulfation of said partially desulfated product.

PRIOR ART

Heparin is a polysaccharide extracted by animal organs, employed for more than lo fifty years as an anticoagulant and antithrombotic agent. Together with heparan sulfate, it belongs to the family of the glycosaminoglycans, consisting of alternate sequences of an uronic acid (iduronic or glucuronic) and glucosamine, variously sulfated depending on the tissue and the animal species from which they have been obtained and, to a certain extent, on the isolation processes too. The structure of heparin may be represented in statistical terms by formula

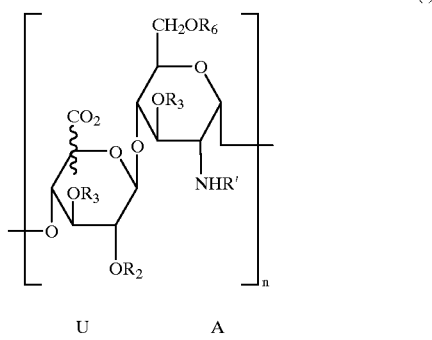

$R = SO_3$ or H
$R' = SO_3$ or Ac where the U units represent the iduronic (IdoA) or glucuronic (GlcA) acid and the. A units represent the N-sulfated (GlcNAc) glucosamine; $R_2$, $R_3$ and $R_6$ represent sulfate groups or hydrogen and R' represents $SO_3$ or Ac. The sequences mostly represented in the heparins used in clinic are those of the trisulfated disaccharide (IdoA2$SO_3$-GlcN$SO_3$6$SO_3$). On the contrary, a minor pentasaccharidic sequence contained only in about one third of the chains forming the common heparins and characterized by a glucosaminic unit sulfated in position 3 (GlcN$SO_3$3$SO_3$) and forming the active site of heparin and heparan sulfate for the antithrombin III is essential for the expression of significant anticoagulant and antithrombotic activities. The 3-O-sulfated glucosamine unit is considered the marker of said active site and the antithrombotic activity, generally expressed by the inhibition capability of the X activated (Xa) and thrombin (IIa) coagulation factors, is correlable with the content percent of said unit in the heparins.

The anticoagulant and antithrombotic properties of heparin and heparan sulfate are also modulated by the length of the polysaccharidic chains composing them. For example the heparins having low molecular weight (LMWH) have lower anticoagulant activity but antithrombotic activity similar to the traditional heparins one, and they are inclined to substitute the latter ones in several therapeutic applications, especially in order to reduce the haemorrhagic risks and other side effects of heparin, such as the thrombocytopenia. In addition, the LMWH are characterized by a bioavailability better than the traditional heparins one when they are administered by subcutaneous route, as it is common in the prevention of the venous thrombosis. (B. Casu Heparin structure, Hemostasis 20/1, 66–73 (1990)); (D. A. Lane, J. Björk, U. Lindall (Ed. s). Heparin and Related Polysaccharides, Plenum Press, New York, 1992).

Since, as above remembered, the pentasaccharidic sequences of heparin mostly responsible of the antithrombotic activity are contained only in about one third of the natural heparin chains, it is of practical interest to strengthen said activity concentrating the chains containing said sequences, or generating new active sites either in the chains which already contain one, or in those ones lacking active sites. The first goal, attainable by affinity chromatography on antithrombin III or (less effectively) by treatment of heparin with cationic resins, is still considered expensive, also because it does not use a substantial (about two thirds) part of the common heparins.

The goal to generate further active sites for antithrombin is not on the other hand attainable by sulfation of heparin with classical methods, which result in structures wherein the active site for antithrombin is masked by an excess of sulfate groups. Even if fortuitously they show an anticoagulant activity greater than the starting heparin one (for the most part by action mechanisms different from the ones mediated by antithrombin), said products are generally less active than heparin as antithrombotic agents, and they may generate undesirable side effects due to the aspecific interactions with other plasmatic proteins. [B. Casu, Structure and biological activity of heparin, Advances Carbohydr. Chem. Biochem. 43, 51–134 (1985)].

On the other hand, attempts to "reconstruct" the active sequences of heparin by resulfation of partially or totally desulfated heparins result in products with a reduced, rather than strengthened, antithrombotic activity. This is due, in particular, to the tendency of the iduronic units to sulfate in position 3 rather than in position 2, and/or to insufficient sulfation in position 3 of the glucosaminic units. [R. N. Rej, K. G. Ludwig-Baxter, A. S. Perlin, Carbohydr. Res. 210, 299–310 (1991)].

SUMMARY OF THE INVENTION

Now we have found a process which makes possible to obtain glycosaminoglycans having high antithrombotic activity in vitro, containing at least 20% of iduronic units sulfated in position 2 and not sulfated in position 3 and at least 30% of sulfaminoglucosaminic units sulfated in position 3 and in position 6, and having a sulfates/carboxyls molar ratio ranging from 2.0 to 3.5. Said process employs as starting materials various kinds of supersulfated glycosaminoglycans and it is characterized by the following steps:
a) preparation of the salt of an organic base of the starting supersulfated glycosaminoglycan;
b) partial solvolytic desulfation of the salt of the organic base of the step a);
c) N-resulfation of the partially desulfated product of the step b);
d) possible 6-O-resulfation of the product of the step c).

The obtained product may be used as an active substance in the preparation of pharmaceutical compositions suitable to the antithrombosis treatment.

DETAILED DESCRIPTION OF THE INVENTION

The characteristics and the advantages of the glycosaminoglycans having high antithrombotic activity according to the present invention and the related preparation process will be mostly illustrated during the following detailed description.

In the process according to the present invention as starting materials may be used several kinds of supersulfated glycosaminoglycans and in particular may be employed: low molecular weight supersulfated heparins (ssLMWH), from 1,500 to 8,000 daltons, high molecular weight supersulfated heparins, from 8,000 to 20,000 daltons, low molecular weight supersulfated heparan sulfates, from 1,500 to 8,000 daltons, high molecular weight supersulfated heparan sulfates, from 8,000 to 25,000 daltons, "biotechnological" supersulfated heparan sulfates and heparins, epimerized and not epimerized, obtained from the N-sulfated K5 polysaccharide. As it is known, the supersulfated glycosaminoglycans are glycosaminoglycans in which all the hydroxylic hydrogens (or the most part of them) have been substituted with $SO_3-$ groups, and they are prepared according to procedures described by various authors (M. L. Wolfrom et al, J. Am. Chem. Soc. 75, 1519 (1953); Nagasawa et al., Carbohydr. Res. 158, 183–190 (1986); EP 214,879 (1986); U.S. Pat. No. 4,727,063; Naggi et al., Biochem. Pharmacol. 36, 1895–1900 (1987); Ogamo et al., Carbohydr. Res. 193, 165–172 (1989)).

The process is carried out according to the following steps:

a) Preparation of the salt of an organic base of the starting supersulfated glycosaminoglycan, said organic base being selected among pyridine, tetramethyl ammonium and tetrabutyl ammonium salts.

The starting supersulfated glycosaminoglycan in form of a sodium salt is dissolved in distilled water and passed through a cationic exchange column.

To the obtained solution the organic base is added at room temperature and in an amount such that pH 9 is reached obtaining the salt which is then lyophilized.

b) Partial solvolytic desulfation of the step a). The organic base salt obtained in the step a) is treated with a solution of an aprotic polar solvent containing methanol or $H_2O$ in a percentage ranging from 5 to 10%, preferably DMSO containing 10% of methanol, with a ratio by weight between this solution and said organic base salt from 50:1 to 100:1.

The obtained solution is heated under stirring at a temperature ranging from 50 to 90° C. for a time ranging from 5 to 480 minutes obtaining the partial desulfation of said salt.

The reaction mixture is then added with water and 0.25 N NaOH to a neutral pH and the product is precipitated by addition of EtOH saturated with sodium acetate. product is then dialyzed through cut-off 2000 membranes and desalted by gel filtration.

c) N-resulfation of the product obtained from the step b).

The product obtained from the step b) is dissolved in an amount of water from 10/0.1 to 10/1 ml/g and the solution is added with $NaHCO_3$ to pH 9 and then trimethylamine sulfur trioxide in an amount by weight equal to said product one. It is heated to 50–60° C. for two hours and then an equal amount of trimethylamine sulfur trioxide is added again and the heating is continued at the same temperature for 24 hours.

The product is precipitated by addition of EtOH saturated with sodium acetate, dialyzed through cut-off 2000 membranes in NaCl solutions first and then in distilled water and finally it is desalted by gel filtration.

d) Possible 6-O-resulfation of the product obtained from the step c). The products which, basing on the NMR analysis result to be desulfated for more than 30% in position 6 of the glucosaminic unit, may be 6-O-resulfated according to known processes (i.e. according to K. Nagasawa, H. Vchiyama and N. Wajiama, Carbohydr. Res. 158 (1986) 183–190).

The obtained product exhibits the following characteristics:

at the least 20% of iduronic units sulfated in position 2 and not sulfated in position 3;

at least 30% of sulfaminoglucosaminic units sulfated in position 3 and in position 6, as in the site active for the antithrombin of the natural heparins;

sulfates/carboxyls molar ratio ranging from 2.0 to 3.5;

anti-Xa activity in vitro ranging from 100 to 150 U/mg.

The content of iduronic units sulfated in position 2 and not sulfated in position 3, and of sulfaminoglucosaminic units sulfated in position 3 has been determined by NMR analysis based on the integration of signals specifically attributable to determined units and determined types of sulfation [E. A. Yates, F. Santini, M. Guerrini, A. Naggi, G. Torri, B. Casu: $^1H$ and $^{13}C$ NMR spectral assignments of the major sequences of twelve systematically modified heparin derivatives, Carbohydr. Res. 294, 15–27 (1996)].

The sulfates/carboxyls molar ratio has been determined by a conductometric method [B. Casu and U. Gennaro: A simple conductometric method for determining the sulfate and carboxylate groups of heparin and chondroitin sulfates, Carbohydr. Res. 39,168–176 (1975)].

The anti-Xa activity in vitro has been determined by a chromogenic method (A. N. Teien et al., Thrombosis Res. 8, 413416, 1976). The present invention refers particularly to glycosaminoglycans belonging to the group consisting of low molecular weight heparins (from 1,500 to 8,000 daltons), high molecular weight heparins (from 8,000 to 18,000 daltons), low molecular weight heparan sulfates (from 1,500 to 8,000 daltons), high molecular weight heparan sulfates (from 8,000 to 25,000 daltons) and heparan sulfates and heparins from the K5 polysaccharide. Thanks to their characteristics, the glycosaminoglycans according to the present invention may be used in mixture with pharmacologically acceptable excipients or diluents, for the preparation of pharmaceutical compositions suitable to the antithrombosis treatment.

The present invention also relates thereby to the therapeutic method for the treatment and the prevention of thrombosis, consisting in the administration of a dose from 1 to 1,500 mg/day of said glycosaminoglycans.

With illustrative aim of the invention the following examples are reported:

DETAILED DESCRIPTION OF THE DRAWINGS

FIG. 1A—$^{13}C$-NMR spectrum of supersaturated low molecular weight heparin (ssLMWH) starting material as described in Example 1a).

Figure 1B:
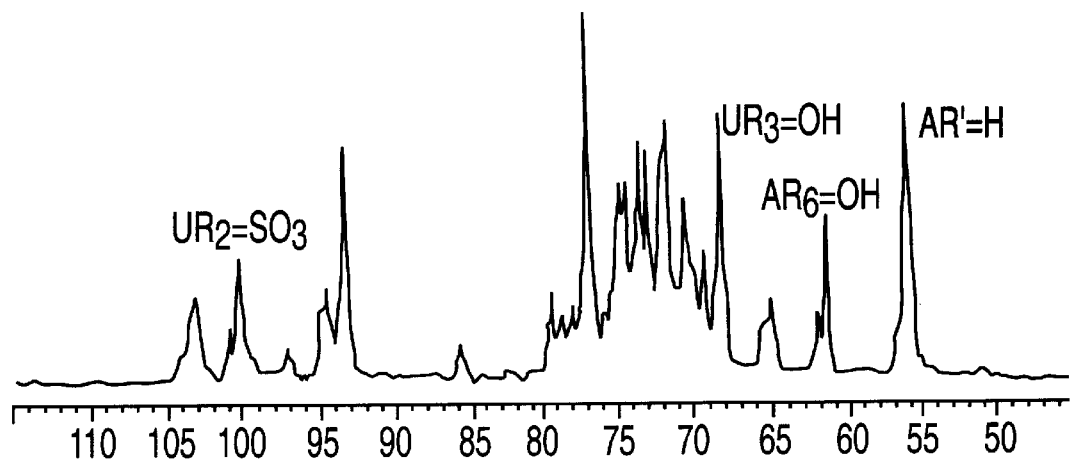

FIG. 1B—$^{13}C$-NMR spectrum of totally N-desulfated and partially 6-O-desulfated ssLMWH as described in Example 1b).

Figure 1C:
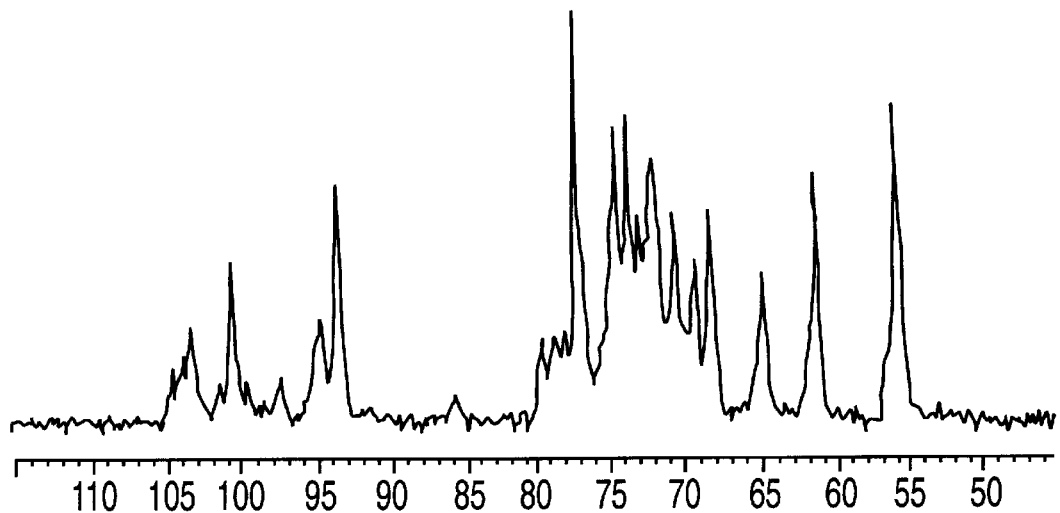

FIG. 1C—$^{13}C$-NMR spectrum of desulfated ssLMWH as described in Example 1b) and with a desulfation time of 30 minutes.

Figure 1D:
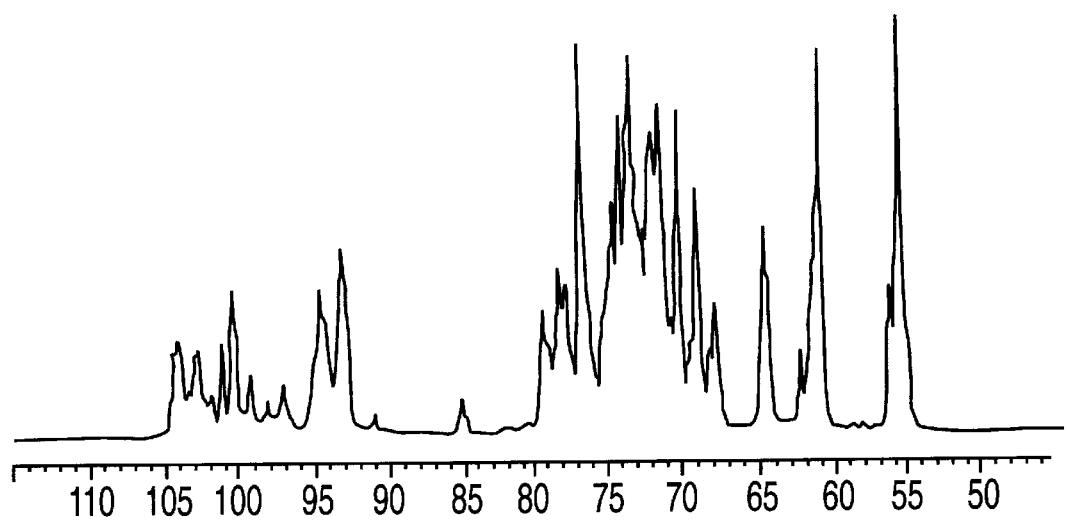

FIG. 1D—$^{13}C$-NMR spectrum of desulfated ssLMWH as described in Example 1b) and with a desulfation time of 45 minutes.

EXAMPLE 1

Preparation of Low Molecular Weight Heparin Having High Antithrombotic Activity a) Preparation of the pyridine salt of a supersulfated low molecular weight heparin (ssLMWH) (G 1074/4)

360 mg of the sodium salt of ssLMWH having a molecular weight equal to 5,000 daltons, obtained from a commercial heparin from swine intestinal mucosa according to the procedure described in the U.S. Pat. No. 4,727,063 and in the publication: Naggi et al., Biochem. Pharmacol. 36, 1895–1900 (1987), having anti-Xa activity=87 U/mg, the $^{13}$C-NMR spectrum of FIG. 1A, have been dissolved in distilled water (30 ml) and passed through a cationic exchange column (AMBERLITE IR 120 in the H$^+$ form). The obtained solution has been taken to pH 9 with pyridine. The so obtained pyridine salt of the supersulfated low molecular weight heparin has been lyophilized.

b) Desulfation of the pyridine salt of the ssLMWH.

The above obtained pyridine salt of the supersulfated low molecular weight heparin has been dissolved in a solution of 10% DMSO/MeOH (25 ml). The solution has been heated under stirring in an oil bath at 80° C. for 15 minutes. At the end of the reaction 15 ml of water have been added and the solution has been neutralized with 0.25 N NaOH. The reaction product has been precipitated by the addition of 60 ml of EtOH saturated with sodium acetate, dialyzed through cut-off 2000 membranes for 48 hours in distilled water and desalted by gel filtration on Sephadex G25. The obtained product exhibits the following characteristics: the $^{13}$C-NMR spectrum (FIG. 1B) shows typical signals from totally N-desulfated (C2NH$_2$:56 ppm) and partially 6-O-desulfated (C6OH:62 ppm) heparin, and the signal at 65 ppm typical of iduronic units not sulfated in position 3 and sulfated in position 2.

c) N-resulfation of the partially desulfated product of the step b) (G 2291)

100 mg of the product obtained in the step b) have been dissolved in 10 ml of water and taken to pH 9 with NaHCO$_3$. Then the same amount by weight of trimethylamine sulfur trioxide (TMA.SO$_3$) has been added and the solution has been heated under stirring in an oil bath at 55° C. After 2 hours a further addition equal by weight of TMA.SO$_3$ has been carried out and it is left to react for 24 hours. At the end of the reaction the mixture has been taken to pH 9.

The sample has been precipitated by addition of 4 volumes of EtOH saturated with sodium acetate, dialyzed through cut-off 2000 membranes for 24 hours in 1 N NaCl, for 24 hours in 0.5 N NaCl and for 24 hours in distilled water, and desalted by gel filtration on Sephadex G25.

The obtained product exhibits the following characteristics:

Sulfates/carboxyls molar ratio: 3.22

Anti-Xa activity: 152 U/mg.

The $^1$H-NMR spectrum confirms the complete N-sulfation.

EXAMPLE 2

(G 2309)

The Example 1 has been repeated, with a reaction time of desulfation equal to 30 min. The product obtained from the desulfation shows the $^{13}$C-NMR spectrum reported in FIG. 1C, with the characteristics described in the point b) of the Example 1.

After the N-resulfation, the obtained product exhibits the following characteristics:

Anti-Xa activity: 110 U/mg.

The $^1$ H-NMR spectrum confirms the complete N-sulfation.

EXAMPLE 3

(G 2301)

a) The Example 1 has been repeated, with a reaction time of desulfation equal to 45 min. The product obtained from the desulfation shows the $^{13}$C-NMR spectrum reported in FIG. 1D, with the characteristics described in the point b) of the Example 1.

After the N-resulfation, the $^1$H-NMR spectrum confirms the complete N-sulfation.

b) The N-resulfated product has been 6-O-resulfated according to the procedure cited in the detailed description.

EXAMPLE 4

The Example 1 has been repeated changing times and temperature of the point b), and precisely operating for 1.5 hours at 65° C. The products obtained from the desulfations exhibit $^{13}$C-NMR spectra analogous to those ones of the FIGS. 1B, 1C, and 1D.

The signal at 65 ppm (typical of the iduronic units desulfated in position 3 and sulfated in position 2) is present in significant amounts, even if lower than those obtained under the conditions of the Example 1 at the point b).

EXAMPLE 5 a) The Example 1 has been repeated with a desulfation temperature equal to 90° C. and a time of 45 min. The product obtained from the desulfation exhibits a $^{13}$C-NMR spectrum with characteristics similar to those described in the point b) of the Example 1. However the signal characteristic of the glucosamine sulfated in position 6 is sensibly lower, and the signal characteristic of the glucosamine not sulfated in said position is sensibly greater, than that one of the spectra of the products obtained at higher temperatures and shorter times.

b) The product has been 6-O-resulfated according to the procedure cited in the detailed description.

EXAMPLE 6

The Example 1 has been repeated, starting from high molecular weight heparin (12,000 daltons) supersulfated treating its pyridine salt in DMF at 55° C. with SO$_3$/pyridine adduct (molar ratio 3:1 with respect to the free hydroxyls) for 5 hours. The obtained product (sulfates/carboxyls molar ratio >3; $^{13}$C-NMR signal at 75 ppm characteristic of the iduronic units sulfated in position 2 not sulfated in position 3) has been N-resulfated as described in the Example 1c.

As illustrated in Table 1 for the low molecular weight heparins, the antithrombotic activity of the obtained products (expressed by the inhibition in vitro of the Xa factor) is noteworthily higher either than the starting supersulfated product one or than the low molecular weight heparins one presently available on the market, used in therapy.

TABLE 1

| | Anti-Xa ACTIVITY* | |
|---|---|---|
| | 1st set | 2nd set |
| LMW-H | — | 100 |
| ssLMWH (G 1074/4) | 100 | — |
| 15' desulfation from G1074/4 (G 2281) | 175 | 162 |
| 30' desulfation from G1074/4 (G 2309) | 125 | 125 |

*U/mg. Normalized values in the first set with respect to the supersulfated low molecular weight heparin (ssLMWH), and in the second set with respect to a mixture 1:1 by weight of the commercial products "Fraxieparin" and "Lovenox" (LMWH).

EXAMPLES 7–17

Description of the used glycosaminoglycans.

Commercial heparin having high molecular weight HMWH (Mw=12,000 Da, anti-Xa activity 192 U/mg) obtained from swine intestinal mucosa (Examples 7, 8, 9, 10)

Commercial heparan sulfate (HS). The ratio between iduronic acid and glucuronic acid varies as a function of the used heparan:
30% iduronic acid, 70% glucuronic acid (Example 11)
40% iduronic acid, 60% glucuronic acid (Example 12)

K5 Polysaccharide (K5-PS) (Examples 13, 14)

Epimerized K5 Polysaccharide (eK5-PS). The degree of epimerization varies as a function of the used eK5-PS:
30% iduronic acid, 70% glucuronic acid (Example 15)
60% iduronic acid, 30% glucuronic acid (Examples 16, 17)

a) Preparation of the supersulfated substrate 1.5 g of the sodium salt of the used substrate have been dissolved in distilled water (30 ml) and passed through a cationic exchange column (AMBERLITE IR 120 in the $H^+$ form). The obtained solution has been taken to pH 9 with a solution of 10% tetrabutyl ammonium hydroxide in ethanol. The so obtained tetrabutyl ammonium salt has been lyophilized. The tetrabutyl ammonium salt of the substrate has been dissolved in DMF (60 ml) and then pyridine sulfur trioxide ($Py.SO_3$) has been added in the amounts of 3 eq. for free hydroxyl and the solution has been heated under stirring in an oil bath at 55° C. overnight. At the end of the reaction 5 ml of water have been added and the reaction product has been precipitated by addition of 200 ml of EtOH saturated with sodium acetate, dialyzed through cut-off 6000–8000 dialysis membranes for 48 hours in distilled water and desalted by gel filtration on Sephadex G25. The obtained products exhibit the following characteristics.

The $^{13}C$-NMR spectra show the signals typical of a completely N-desulfated (A2NH2) C2:56 ppm glucosamine and totally 6-O-sulfated (A6S) C6 69 ppm, and of uronic units sulfated in position 2 and 3 on the same residue (U2,3S) C1 Å 101.5 ppm). The sulfation degree obtained on the uronic units changes as a function of the used glycosaminoglycan. The data obtained for the obtained supersulfated products are described in Table 2.

b) Preparation of the pyridine salt of the supersulfated substrate (ssHMWH). 1 g of the sodium salt obtained by the process described in the step a) has been dissolved in distilled water (30 ml) and passed through a cationic exchange column (AMBERLITE IR 120 in the $H^+$ form). The obtained solution has been taken to pH 9 with pyridine. The pyridine salt of the so obtained supersulfated substrate has been lyophilized.

c) Desulfation of the pyridine salt of the supersulfated substrate 100 mg of the pyridine salt obtained as described above have been dissolved in a solution of DMSO/MeOH 10% (10 ml). The solution has been heated under stirring (in an oil bath) using the temperatures and times described in Table 3. At the end of the reaction 5 ml of water have been added and the reaction product has been precipitated by the addition of 100 ml of EtOH saturated with sodium acetate, dialyzed through cut-off 6000–8000 dialysis membranes for 48 hours in distilled water and desalted by gel filtration on Sephadex G25.

The obtained products exhibit the characteristics described in Table 3.

d) N-resulfation of the partially desulfated products obtained from the step c)

100 mg of the product obtained in the step c) have been dissolved in 10 ml of water and taken to pH 9 with $NaHCO_3$. Then the same amount by weight of trimethylamine sulfur trioxide ($TMA:SO_3$) has been added and the solution has been heated under stirring in an oil bath at 55° C. After 2 hours a further addition equal by weight of $TMA.SO_3$ has been carried out and it has been left to react for 24 hours. At the end of the reaction the 5 ml of water have been added and the reaction product has been precipitated by the addition of 50 ml of EtOH saturated with sodium acetate, dialyzed through cut-off 6000–8000 dialysis membranes for 48 hours in distilled water and desalted by gel filtration on Sephadex G25. The $^{13}C$-NMR spectra show the complete N-resulfation of the obtained products. Of the obtained products the sulfation degree expressed as sulfates/carboxyls (DS) ratio, the molecular weight (Mw) and the biological activities (aPTT, anti IIa and anti Xa) have been determined. The obtained data are described in Table 4.

TABLE 2

Description of the supersulfated glycosaminoglycans obtained as described in point a). In the first column of the Table it is pointed out in which Examples such products are used

| Example | Substrate | GAG | % A6S | % UOH + U3S | % U2S + U2, 3S |
|---|---|---|---|---|---|
| 7, 8, 9, 10 | ss-HMWH | 2522 | 100 | 0 | 100 |
| 11 | ss-LMWH | 1079/4 | 100 | 5 | 95 |
| 12 | ss-HS | 2460 | 100 | 50 | 50 |
| 13 | ss-HS | 2648 | n.a. | n.a. | n.a. |
| 14–15 | ss-K5-PS | 2444 | 100 | 0 | 100 |
| 16 | ss-eK5-PS | 2611 | 100 | 0 | 100 |
| 17 | ss-eK5-PS | 2721 | n.a. | n.a. | n.a. |

TABLE 3

Description of the used reaction conditions (substrate, temperatures and times) and characterization of the obtained products

| Ex. | Substrate | GAG | T ° C. | th | % A6S | % UOH + U3S | % I2S | % G3S |
|---|---|---|---|---|---|---|---|---|
| 7 | HMWHep | 2541A | 65 | 4 | 39 | 35 | 54 | n.a. |
| 8 | HMWHep | 2632A | 65 | 8 | 30 | 44 | 54 | n.a. |
| 9 | HMWHeP | 2632B | 65 | 16 | 5 | 50 | 54 | n.a. |
| 10 | HMWHep | 2541B | 65 | 24 | 5 | 59 | 42 | n.a. |
| 11 | LMWHep | 2474 | 65 | 4 | 25 | 54 | 46 | n.a. |
| 12 | HS | 2556 | 65 | 4 | 50 | 60 | 20 | 25 |
| 13 | HS | 2734 | 80 | 30' | n.a. | n.a. | n.a. | n.a. |
| 14 | K5-PS | 2451A | 80 | 45' | 40 | 48 | — | 52 |
| 15 | K5-PS | 2451B | 80 | 75' | 20 | 50 | — | 50 |
| 16 | eK5-PS | 2622 | 65 | 4 | 30 | n.a. | n.a. | 20 |
| 17 | eK5-PS | 2737 | 80 | 30' | n.a. | n.a. | n.a. | n.a. |

TABLE 4

Description of the products obtained after the N-resulfation and their characterization

| Ex. | GAG | DS | Mw | aPTT | anti IIa | anti Xa |
|---|---|---|---|---|---|---|
| 7 | 2557 | 1.8 | 12000 | n.a. | n.a. | 110 |
| 8 | 2632BNS | n.a. | 10300 | n.a. | n.a. | 99 |

TABLE 4-continued

Description of the products obtained after the
N-resulfation and their characterization

| Ex. | GAG | DS | Mw | aPTT | anti IIa | anti Xa |
|---|---|---|---|---|---|---|
| 9 | 2632ANS | n.a. | 7600 | n.a. | n.a. | 7 |
| 10 | 2565 | 1 | 11000 | n.a. | n.a. | 3 |
| 11 | 2374NS | 1.5 | 7400 | 10 | 273 | 130 |
| 12 | 2556NS | n.a. | n.a. | 70 | 1230 | 65 |
| 13 | 2734NS | n.a. | n.a. | n.a. | n.a. | n.a. |
| 14 | 2459A | 2.4 | n.a. | 97 | 470 | 10 |
| 15 | 2459B | 2.3 | n.a. | 32 | 114 | 5 |
| 16 | 2822NS | n.a. | n.a. | 48 | 500 | 13 |
| 17 | 2737NS | n.a. | n.a. | n.a. | n.a. | n.a. |

What is claimed is:

1. A process for the preparation of glycosaminoglycans having an anti-Xa activity in vitro from 100 to 150 U/mg, containing at least 20% of iduronic units sulfated in position 2 and not sulfated in position 3 and at least 30% of sulfaminoglucosaminic units sulfated in position 3 and in position 6, and having a sulfates/carboxyls molar ratio ranging from 2.0 to 3.5, starting from glycosaminoglycans in which the glucosamine units are completely N-desulfated and totally 6-O sulfated and the uronic units are sulfated from 50% to 100% in the positions 2 and 3, wherein said process comprises:
   a) preparation of a salt of an organic base of the starting glycosaminoglycans;
   b) partial solvolytic desulfation of the salts of the step a) by treatment with an aprotic polar solvent containing methanol or water at a temperature ranging from 50 to 80° C. for a time ranging from 5 to 480 minutes;
   c) N-resulfation of the partially desulfated product of step b);
   d) optional 6-0 resulfation of the product of step c).

2. The process as claimed in claim 1, wherein said starting glycosaminoglycan is selected from the group consisting of heparins having a molecular weight from 1,500 to 18,000 daltons, heparan sulfates having a molecular weight from 1,500 to 25,000 daltons and heparan sulfates and heparins obtained from the N-sulfated K5 polysaccharide.

3. The process as claimed in claim 1, wherein said preparation of step a) is carried out by treating a water solution of the starting glycosaminoglycan in form of sodium salt with an organic base selected from pyridine, tetramethyl ammonium and tetrabutyl ammonium salts in an amount that pH 9 is reached, at room temperature.

4. The process as claimed in claim 1, wherein said polar solvent of step b) consists of DMSO containing 10% of methanol with a weight ratio to the salt of said organic base from 50:1 to 100:1.

5. The process as claimed in claim 1, wherein said N.-resulfation of step c) is carried out by treating an aqueous solution of the product obtained in step b) with trimethylamine sulfur trioxide in an amount by weight equal to said product one, at pH 9, heating to 50–60° C3 and adding subsequently again an equal amount of trimethylamine sulfur trioxide.

* * * * *